(12) United States Patent
Zardini

(10) Patent No.: US 8,679,258 B2
(45) Date of Patent: Mar. 25, 2014

(54) WASHING PLANT

(75) Inventor: Fabio Zardini, Castelfranco Veneto (IT)

(73) Assignee: Steelco SpA, Riese Pio X (IT)

( * ) Notice: Subject to any disclaimer, the term of this patent is extended or adjusted under 35 U.S.C. 154(b) by 502 days.

(21) Appl. No.: 12/676,327

(22) PCT Filed: Aug. 22, 2008

(86) PCT No.: PCT/EP2008/061020
§ 371 (c)(1),
(2), (4) Date: Mar. 3, 2010

(87) PCT Pub. No.: WO2009/030599
PCT Pub. Date: Mar. 12, 2009

(65) Prior Publication Data
US 2010/0206335 A1 Aug. 19, 2010

(30) Foreign Application Priority Data

Sep. 4, 2007 (IT) .............................. UD2007A0155

(51) Int. Cl.
*B08B 3/00* (2006.01)
(52) U.S. Cl.
USPC .............. 134/19; 134/105; 134/124; 134/126
(58) Field of Classification Search
USPC ........... 134/56 D, 57 D, 58 D, 105, 124, 126, 134/129, 132, 134
See application file for complete search history.

(56) References Cited

U.S. PATENT DOCUMENTS

| 1,734,585 | A | * | 11/1929 | Ladewig et al. | ................. | 134/62 |
| 3,896,827 | A | * | 7/1975 | Robinson | ......................... | 134/10 |
| 4,313,451 | A | * | 2/1982 | Vilen | .............................. | 134/47 |
| 5,464,032 | A | * | 11/1995 | Litterst | ........................... | 134/72 |

(Continued)

FOREIGN PATENT DOCUMENTS

| DE | 1431687 A1 | 11/1968 |
| DE | 2208802 A1 | 8/1973 |

(Continued)

OTHER PUBLICATIONS

Machine translation of Abstract of JP 2007217079 to Kutoku et al., Aug. 2007.*

(Continued)

*Primary Examiner* — Michael Barr
*Assistant Examiner* — Benjamin L Osterhout
(74) *Attorney, Agent, or Firm* — Novak Druce Connolly Bove + Quigg, LLP

(57) ABSTRACT

Washing plant to perform a washing cycle of objects providing at least a pre-wash operation and a washing and heat disinfecting the objects operation. The plant includes a first battery of pre-wash units, in series one after the other along a first alignment axis and a second battery of washer and heat disinfection machines along a second alignment axis, different from the first alignment axis to operate parallel with each other and perform object washing and heat disinfecting. The second battery is able to receive, along a feed direction transverse to the second alignment axis, the objects subjected to pre-wash exiting from the first battery along the first axis alignment. The second battery feed direction is also transverse to the first alignment axis. Movement members are provided to divert the objects exiting from the first battery and direct them, aligned with the direction of feed, towards the second battery.

9 Claims, 2 Drawing Sheets

(56) References Cited

U.S. PATENT DOCUMENTS

| | | | |
|---|---|---|---|
| 6,959,714 | B1 | 11/2005 | Hakansson et al. |
| 7,459,706 | B2 | 12/2008 | Fontcuberta et al. |
| 2002/0153021 | A1* | 10/2002 | Audet .............................. 134/1 |
| 2004/0159336 | A1* | 8/2004 | Feistmantl ...................... 134/18 |
| 2004/0238017 | A1* | 12/2004 | Kuhl ................................ 134/72 |
| 2006/0186350 | A1 | 8/2006 | Fontcuberta et al. |
| 2007/0205081 | A1 | 9/2007 | Kyutoku et al. |
| 2008/0098666 | A1 | 5/2008 | Larsson |

FOREIGN PATENT DOCUMENTS

| | | | |
|---|---|---|---|
| EP | 1 685 853 | A1 | 8/2006 |
| EP | 1 237 460 | B1 | 9/2006 |
| EP | 1237460 | B1 | 9/2006 |
| EP | 1 787 662 | A1 | 5/2007 |
| EP | 1 787 731 | A1 | 5/2007 |
| EP | 1787662 | A1 | 5/2007 |
| EP | 1787731 | * | 5/2007 |
| FR | 2 803 528 | | 7/2001 |
| JP | 2007217079 | A * | 8/2007 |
| JP | 20027217079 | | 8/2007 |
| WO | 01/34015 | A1 | 5/2001 |
| WO | 2006/078197 | A1 | 7/2006 |

OTHER PUBLICATIONS

E1-a.pdf, drawings showing a full layout (p. 1) and part of the layout (p. 2) of a washing plant delivered by Getinge Disinfection AB (Aktiebolag) to B. Braun Medical CSSD (Lyon-Chassieu), 2001.

E1-b.pdf, In the Opposition Against European Patent No. 2200660 B1, Witness Declaration by Mr Roland Karlsson, Oct. 11, 2013.

Notice of opposition to a European Patent EP2200660 dated Oct. 14, 2013.

* cited by examiner

WASHING PLANT

CROSS REFERENCE TO RELATED APPLICATIONS

This application is a §371 National Stage Application of International Application No. PCT/EP2008/061020, filed on 22 Aug. 2008, claiming the priority of Italian Patent Application No. UD2007A000155 filed on 4 Sep. 2007.

FIELD OF THE INVENTION

The present invention concerns a plant for washing objects, for example medical instruments for hospital wards, operating rooms, laboratories and the pharmaceutical industry, comprising a first battery of pre-wash machines aligned according to a determinate axis of alignment so as to operate in series, at least a second battery of washer machines, aligned so as to operate in parallel, and a movement device able to allow the objects to be washed to pass from the first to the second battery.

BACKGROUND OF THE INVENTION

It is known that, usually, hospital structures comprise a washing plant in order to effect a pre-wash, wash, heat disinfection and sterilization of objects, such as for example instruments used in the operating rooms and hence potentially infected and not sterile, before being able to re-use them.

In particular, known washing plants are normally divided into several sectors, isolated from each other for hygienic reasons and called, respectively, the "dirty" sector, or reception sector, the "clean" sector and the "sterile" sector.

The dirty objects to be subjected to the various treatments arrive in the first sector, or dirty sector. The treatments carried out are generally a pre-wash with cold water only, a possible wash in an ultra-sound bath, a wash with hot water and possible detergents, the necessary rinses, a heat disinfection and a final drying. In particular, the heat disinfection, which is a particular type of wash, is effected with hot water, usually at a temperature comprised between about 90° C. and about 93° C.

Usually the pre-wash is effected by means of a battery of suitable pre-wash machines or units, for example two or three, disposed aligned according to a determinate axis of alignment, so as to operate in series with one another.

Heat disinfection, on the other hand, is effected in a battery of suitable washer machines, for example five or six, according to the necessary production, aligned according to a respective axis of alignment, so as to operate in parallel with each other.

The objects to be washed are picked up at exit from the last pre-wash unit and fed to the washer and heat disinfection machine available at that moment.

Each washer and heat disinfection machine, since it is operating in parallel with the other washer machines, and consists of a washing chamber with an aperture facing towards the dirty side and an opposite aperture facing towards the clean side, must be fed in a direction orthogonal to its axis of alignment with the other washer and heat disinfection machines. On the contrary, in the pre-wash machines, since they operate in series, the direction of feed coincides with the axis of alignment along which the pre-wash battery develops.

Normally therefore, the second washer and heat disinfection battery is disposed downstream of the pre-wash battery and with its axis of alignment perpendicular to the axis of alignment of the pre-wash battery. Therefore, the axis of alignment of the pre-wash units is orthogonal to the axis of alignment of the washer and heat disinfection machines. In this way the objects exiting from the last pre-wash unit are ready to be directed directly to the washer and heat disinfection machines.

Examples of embodiments of such washing plants are to be found in the European patent applications no 06124039.6 and no 06124017.2 in the name of the present Applicant.

After they have been heat disinfected and dried, the objects pass to the second clean sector where they are possibly packed and, from here, they are fed to a battery of sterilization machines which provide to sterilize them, generally autoclaves that operate in parallel and typically are aligned in a direction parallel to the washing and heat disinfection battery.

The objects thus sterilized pass to the subsequent third sterile sector where they are stored or returned to the operating room for use.

One disadvantage of known washing plants is that, to effect at least the pre-wash and the washing and heat disinfection, they have a very high bulk when installed.

Purpose of the present invention is to achieve a washing plant which does not occupy much space, which is compact and allows easy passage from the battery of pre-wash units to the battery of washer and heat disinfection machines.

The Applicant has devised, tested and embodied the present invention to overcome the shortcomings of the state of the art and to obtain these and other purposes and advantages.

SUMMARY OF THE INVENTION

The present invention is set forth and characterized in the independent claim, while the dependent claims describe other characteristics of the invention or variants to the main inventive idea.

In accordance with the above purpose, a washing plant according to the present invention is used to effect at least a cycle for washing objects, which provides at least a pre-wash operation and a washing and heat disinfection operation.

The plant according to the present invention comprises a first battery of pre-wash units disposed in series with each other along a first axis of alignment and a second battery of washer and heat disinfection machines disposed along a second axis of alignment, different from the first axis of alignment and able to operate in parallel with each other in order to effect the washing and heat disinfection.

The second battery is able to receive, in a direction of feed transverse to the second axis of alignment, the objects subjected to pre-wash at exit from the first battery along the first axis of alignment.

According to a characteristic feature of the present invention, the direction of feed of the second battery is also transverse to the first axis of alignment of the first battery, movement means being provided in order to divert the objects exiting from the first battery so as to direct them towards the second battery, aligned with the direction of feed of the machines of the second battery.

According to a characteristic of the present invention, the second axis of alignment of the second battery is substantially parallel to the first axis of alignment of the first battery.

Alternatively, the second axis of alignment could be more or less inclined, but not perpendicular, to the first axis of alignment, so as to reduce in any case the bulk occupied by the installation of the plant according to the invention.

According to another advantageous feature of the present invention, the direction of feed of the second battery is substantially perpendicular to the first axis of alignment of the first battery.

According to a variant, the movement means comprises a rotating table able to rotate the objects exiting from the first battery of pre-wash units in order to direct them towards the second battery of washer and heat disinfection machines.

In this way, a washing plant is achieved that takes up little space, is compact and, thanks to the movement means provided, allows easy passage from the battery of pre-wash units to the battery of washer and heat disinfection machines.

In fact, the second battery is no longer disposed perpendicular to the exit from the pre-wash battery, as in the state of the art, but adjacent and advantageously parallel to it.

The whole transverse bulk that the battery of washer and heat disinfection machines normally occupies in washing plants of a known type, with the present invention on the contrary is distributed advantageously parallel and adjacent to the direction of development of the first pre-wash battery.

Possible sterilization machines, normally provided downstream of the heat disinfection battery, are also disposed along an axis of alignment parallel to the axis of alignment of the first pre-wash battery.

In this way we have a considerable containment of the sizes of the washing plants which, with the present invention, can be installed even in small premises, which normally would not allow this type of installation, except with an intervention to enlarge the premises, with the obvious additional costs.

In this way we also have a reduction in the sizes of the premises that have to be kept constantly in a condition of hygiene and/or sterility, with considerable economic and management advantages.

BRIEF DESCRIPTION OF THE DRAWINGS

These and other characteristics of the present invention will become apparent from the following description of a preferential form of embodiment, given as a non-restrictive example with reference to the attached drawings wherein.

DETAILED DESCRIPTION OF A PREFERENTIAL FORM OF EMBODIMENT

Figure 1:
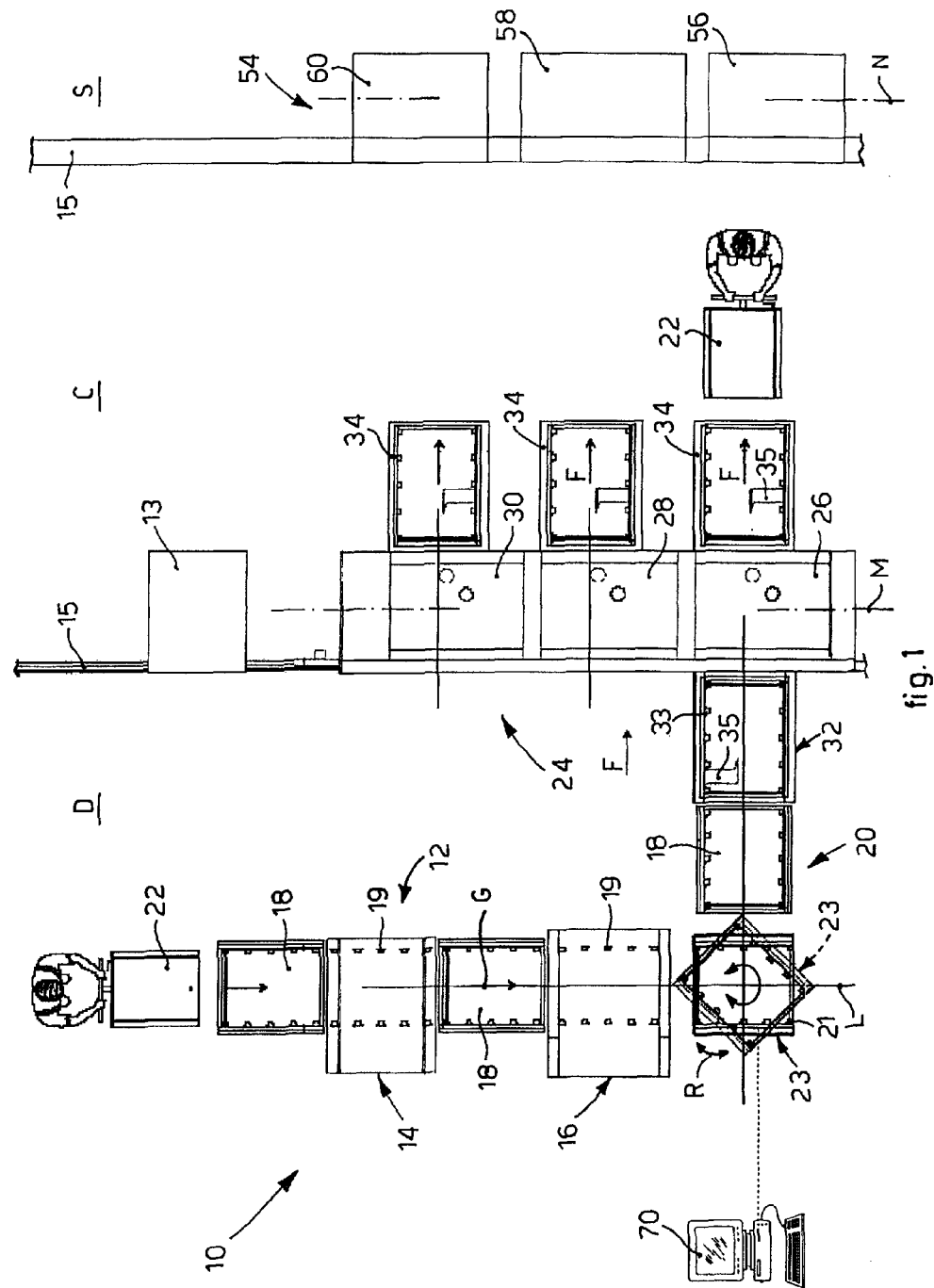
FIG. 1 is a schematic plane view of a washing plant according to the present invention.

With reference to FIG. 1, a washing plant 10 according to the present invention is used to effect the complete treatment of pre-wash, wash, heat disinfection and sterilization of instruments arriving from hospital wards, operating rooms, laboratories and the pharmaceutical industry.

The plant 10 provides three sectors, divided for example by walls 15, possibly put selectively into communication by means of a pass through 13, in particular a dirty sector D, where the dirty instruments are received, a clean sector C, downstream of the heat disinfection, and a sterile sector S, downstream of sterilization.

The plant 10 comprises, in the dirty sector D, a first battery 12 consisting of two pre-wash units 14 and 16, respectively to wash with cold water and in an ultra-sound bath, aligned in series along a first axis of alignment L. It is clear that the first wash battery 12 can also have only one pre-wash unit, or more than two pre-wash units, which perform cold pre-wash, wash with possible chemical detergents and/or wash in an ultrasound bath, and disposed in different combinations and sequences, according to needs.

Between the dirty sector D and the clean sector C, the plant 10 also comprises a second battery of washer machines 26, 28 and 30, also aligned along a second axis of alignment M, substantially parallel to the first axis of alignment L.

Finally, between the clean sector C and the sterile sector S, the plant 10 provides sterilization autoclaves 56, 58 and 60, aligned along a third axis of alignment N, also parallel to the first axis of alignment L.

The pre-wash units 14 and 16 operate in series, whereas the washer machines 26, 28 and 30 operate in parallel, like the sterilization autoclaves 56, 58 and 60.

By operate in series we mean that the objects that exit from a pre-wash unit face directly towards the entrance to the pre-wash unit immediately following, and thus constitute the objects that enter into the following pre-wash unit, except for the last pre-wash unit.

By operate in parallel we mean that the washer and heat disinfection machines are adjacent and have their respective entrance apertures to the internal washing chambers disposed in parallel with each other and on the same plane, so that the objects enter into a selected one of the washer and heat disinfection machines.

This means that the direction of travel and feed of the instruments to be washed along the first battery 12, indicated by the arrows G, substantially coincides with the first axis of alignment L along which the pre-wash units 14 and 16 are aligned, whereas the direction of travel and feed of the instruments to be washed along the second battery 24, indicated by the arrows F, is substantially perpendicular to the second axis of alignment M along which the washer machines 26, 28 and 30 are aligned.

Inside the pre-wash units 14 and 16 rollerways 19 are provided, which allow to move the baskets, guaranteeing continuity of passage along the first battery 12, along the first axis of alignment L and in the direction indicated by the arrows G.

In particular, the pre-wash unit 14 which is disposed at the head of the first battery 12 is fed with a basket carrying the instruments to be washed, by means of a rollerway 18 in turn loaded by means of a manual trolley 22.

The pre-wash unit 14 subjects the instruments to washing in cold water and at exit, by means of another rollerway 18, directs them to the pre-wash unit 16 that performs the ultra-sound bath.

At exit from the pre-wash unit 16 a movement device 20 is provided, which deflects the basket by 90° from the first axis of alignment L in order to direct them, aligned with the direction of feed F, towards the second washing and heat disinfection battery 24. Thanks to the movement device 20, the objects exiting from the end of the first battery 12 are subjected to an elbow-shaped diversion, coherent with the disposition of the second battery 24.

In this way, the part of the plant 10 associated with the dirty sector D comprises three segments, of which two parallel, corresponding to the pre-wash battery 12 and the washing and heat disinfection battery 24, and a perpendicular segment which connects the two parallel segments, corresponding to the movement device 20.

Figure 2:
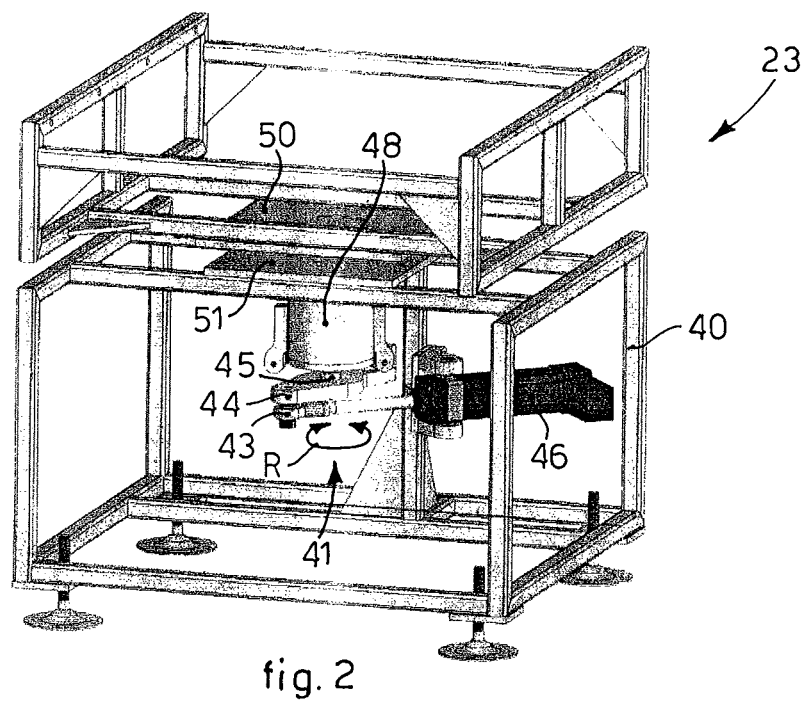
FIG. 2 is a perspective view of a part of the washing plant according to the present invention, in a first operating condition.

In particular, the movement device 20 comprises a rotating table 23, able to rotate on itself as indicated by the arrow R in FIGS. 1 and 2, and a rollerway 18 of the fixed type and a translatable trolley 32 provided with a rollerway 33 and able to translate parallel to the second axis of alignment M, opposite the entrance to the washer machines 26, 28 and 30.

The rotating table 23 allows to rotate the basket carrying the instruments, at exit from the pre-wash unit 16, by 90° with respect to the direction of feed indicated by the arrow F, in order to direct it towards the second battery 24.

At this point, the basket carrying the instruments is opposite the washer machine 26 and is transported, by means of the intermediate rollerway 18, onto the translatable trolley 32.

Once positioned on the translatable trolley 32, the basket is located by the latter in correspondence with the washer machine 26, 28, 30 free at that moment and able to be used for washing.

Between the rotating table 23 and the translatable trolley 32 a store or accumulation sector can be provided, not shown in the drawings, in which the baskets carrying the instruments already subjected to pre-wash and which are to be sent to washing and heat disinfection can be accumulated.

At the end of heat disinfection, the basket with the instruments exits into the clean sector C, by means of a dedicated and fixed rollerway 34, and is located on a manual trolley 22 to be transported to the sterilizing machines 56, 58 and 60.

In order to facilitate and make almost automatic the entrance and exit into/from the washer machines 26, 28 and 30, both the translatable rollerway 32 and the rollerway 34 are provided with a mechanical arm 35 of the selectively mobile type, which respectively thrusts and extracts the basket carrying the instruments.

The operational synchrony and the management of the cycles of pre-wash and wash is managed automatically by means of a control unit 60. In particular, the rotation of the rotating table 23 is automated and synchronized at least with the pre-wash cycle, while the movement of the translatable trolley is automated and synchronized at least with the washing and heat disinfection cycle.

Figure 3:
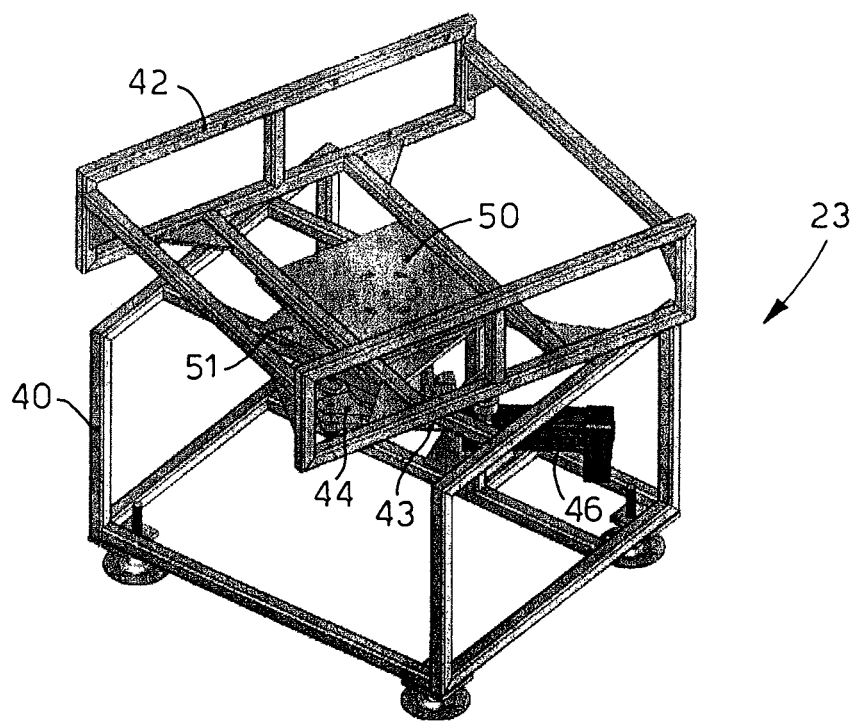
FIG. 3 is a perspective view of the part of the washing plant in FIG. 2, in a second operating condition.

FIGS. 2 and 3 show schematically, in a form of embodiment given as a non-restrictive example, the rotating table 23, respectively in a first operating condition, not rotated, and a second operating condition, rotated by a certain angle.

In this case, the rotating table 23 comprises a fixed frame 40 that functions as a lower support, and a rotary frame 42, located above the fixed frame 40. The rollerway 21 is mounted on the rotary frame 42, represented for convenience only in FIG. 1.

Both the frame 40 and the frame 42 comprise respective attachment plates 50 and 51 of the horizontal type and parallel with each other, the purpose of which will be clarified later in the description.

A linear actuator 46 of the hydraulic type is mounted on the frame 40, having a rod 43 mobile telescopically for a predetermined travel, while on the plate 51, in particular on its lower face, a drum 48 is mounted, bearing centrally a cylinder 45 able to rotate around its own axis and attached at the upper part to the plate 50. The cylinder 45, in substance, connects rotatably the rotary frame 42 to the fixed frame 40.

At the lower part, the cylinder 45 is keyed onto a lever 44, which has one end constrained to the rod 43 of the linear actuator 46.

The linear motion of the linear actuator 46, in particular the telescopic extension of the rod 43 suitably commanded and controlled by the control unit 50, determines the rotation of the lever 44 and consequently of the cylinder 45 and the plate 50 solid therewith. The entity of the travel of the rod 43 of the linear actuator 46 is directly correlated to the angle of rotation to be imparted to the frame 42. All this leads to the rotation, in this case by about 90°, of the rotary frame 42 and hence of the rollerway 21 and the basket with the instruments to be washed.

As we said, the embodiment of the rotating table 23 as shown in FIGS. 2 and 3 is not to be understood as restrictive for the present invention, since according to the present invention any other mechanism could be used which allows to divert from the first axis of alignment L the basket carrying the instruments at exit from the pre-wash unit 16 in order to feed it in the direction of feed F. It is thus possible to provide a rotation mechanism able to determine the rotation on itself of the basket carrying the instruments, in order to direct it correctly towards the second battery 24. For example, an elbow-shaped rollerway could be provided, with a diversion wall, fixed or mobile.

It could also be provided not to rotate the basket carrying the instruments and to feed it directly to one of the washer machines, with the orientation that it possesses at the moment it leaves the unit 16, for example by means of a thruster and a rectilinear rollerway which operate along the direction of feed F.

It is clear that modifications and/or additions of parts may be made to the washing plant 10 as described heretofore, without departing from the field and scope of the present invention.

For example, the linear actuator 46 of the rotating table 23 could be of the oil-dynamic type or the pneumatic type.

Furthermore, instead of rollerways, the present invention could provide conveyor belts, belts, chains or similar movement devices, according to necessity.

It is also clear that, although the present invention has been described with reference to specific examples, a person of skill in the art shall certainly be able to achieve many other equivalent forms of washing plant, having the characteristics as set forth in the claims and hence all coming within the field of protection defined thereby.

The invention claimed is:

1. A washing plant to perform at least a washing cycle of objects that provides at least a pre-wash operation and an operation for the washing and heat disinfection of the objects, comprising:

a first battery of pre-wash units, disposed in series one after the other along a first axis of alignment, wherein the first battery of pre-wash units are arranged such that objects that exit from a pre-wash unit face directly towards the entrance to the pre-wash unit immediately following;

a second battery of washer and heat disinfection machines disposed along a second axis of alignment, different from the first axis of alignment and the washer and heat disinfection machines arranged to operate in parallel with each other to perform the washing and heat disinfection of said objects, the second battery being arranged to receive, along a direction of feed transverse to the second axis of alignment, the objects subjected to pre-wash exiting from the first battery along the first axis of alignment, wherein the first axis of alignment is substantially parallel, or at most slightly inclined, with respect to the second axis of alignment, the direction of feed of the second battery being also transverse to the first axis of alignment, and a rotating table and a rollerway of the fixed type disposed downstream from the rotating table, said rotating table being configured to receive the objects exiting the first battery along the first axis of alignment, rotate the objects exiting from the first battery of pre-wash units along the first axis of alignment, and to direct them towards the second battery of washer and heat disinfection machines along the direction of feed via said rollerway, wherein said rollerway is operatively aligned with the direction of feed.

2. The washing plant as in claim 1, wherein the direction of feed is comprised of a component of travel along which the objects are made to translate parallel to the second axis of alignment, opposite the entrance to the heat disinfection machines and a component of feed of the objects to be washed into the heat disinfection machines, wherein said component of feed is transverse to the first axis of alignment.

3. The washing plant as in claim 1, wherein the direction of feed is substantially perpendicular to the first axis of alignment.

4. The washing plant as in claim 1, wherein the rotating table is able to rotate by about 90° the objects exiting from the first battery of pre-wash units towards the second battery.

5. The washing plant as in claim 1, wherein the rotating table comprises a first supporting frame of the fixed type and a second supporting frame of a rotary type, located above the first supporting frame and on which the objects to be subjected to the washing cycle are positioned, a rotation member being provided to allow the selective rotation of the second supporting frame with respect to the first supporting frame.

6. The washing plant as in claim 5, wherein the rotation member comprises a linear actuator mounted on the first supporting frame and a lever having one end hinged to the linear actuator to be rotary and is attached to a cylinder, the cylinder being in turn solidly connected to a plate attached to the second supporting frame.

7. The washing plant as in claim 1, wherein the movement means comprises a translatable trolley, downstream of the rotating table and operatively aligned with the direction of feed, which is able to translate, in front of the second battery, along a direction parallel to the second axis of alignment.

8. The washing plant as in claim 1, further comprising a third battery of sterilization machines, able to sterilize the objects subjected to washing and heat disinfection in the second battery and disposed along a third axis of alignment, parallel to the second axis of alignment.

9. A method to use the washing plant of claim 1 to perform at least a washing cycle of objects comprising:
- a pre-washing step comprising a plurality of pre-washing operations in series, one after the other along a first axis of alignment, in said first battery of pre-wash units, disposed in series one after the other along a first axis of alignment, wherein the first battery of pre-wash units are arranged such that object that exit from a pre-wash unit face directly towards the entrance to the pre-wash unit immediately following; and
- a washing and heat disinfection step, within said second battery of washer and heat disinfection machines disposed along a second axis of alignment, different from the first axis of alignment, comprising a plurality of washing and heat disinfection operations performed in parallel along a second axis of alignment,
- wherein said objects are moved along said first axis of alignment in a direction substantially parallel, or at most slightly inclined, with respect to the second axis of alignment,
- then said objects are rotated by said movement means to direct them, aligned a direction of feed, towards the washing and heat disinfection operations, and
- then said objects are fed, along said direction of feed, to be subjected to the washing and heat disinfection step along the second axis of alignment.

* * * * *